(12) United States Patent
Martín et al.

(10) Patent No.: US 6,620,433 B2
(45) Date of Patent: Sep. 16, 2003

(54) DISPERSIBLE AND SOLUBLE GALENIC PARACETAMOL FORMULATION, METHOD FOR ITS PREPARATION AND ITS APPLICATIONS

(75) Inventors: Luis Carvajal Martín, Madrid (ES); Juan Carlos Asensio Asensio, Zaragoza (ES); Francisco Javier Sevilla Tirado, Zaragoza (ES)

(73) Assignee: Laboratorios Belmac, S.A., San Sebastian de los Reyes (ES)

( * ) Notice: Subject to any disclaimer, the term of this patent is extended or adjusted under 35 U.S.C. 154(b) by 0 days.

(21) Appl. No.: 10/188,680

(22) Filed: Jul. 3, 2002

(65) Prior Publication Data

US 2002/0197312 A1 Dec. 26, 2002

Related U.S. Application Data

(63) Continuation of application No. PCT/ES01/00402, filed on Oct. 24, 2001.

(30) Foreign Application Priority Data

Nov. 3, 2000 (ES) .......................... P200002653

(51) Int. Cl.[7] .............................. A61K 9/46; A61K 9/16; A61K 31/167; A61P 29/00
(52) U.S. Cl. ....................... 424/465; 424/489; 424/464; 424/470; 424/44
(58) Field of Search ................. 424/484, 489, 424/490, 464, 466, 465, 44

(56) References Cited

U.S. PATENT DOCUMENTS

| 4,309,408 A | * | 1/1982 | Pathak et al. ................. 424/44 |
| 4,614,648 A | | 9/1986 | Bru |
| RE33,086 E | | 10/1989 | Bru |
| 4,942,039 A | | 7/1990 | Duvall et al. |
| 6,159,505 A | * | 12/2000 | Piper ........................... 424/679 |
| 2002/0127184 A1 | * | 9/2002 | Selim ........................... 424/44 |

FOREIGN PATENT DOCUMENTS

| EP | 418564 | 3/1991 |
| EP | 1004292 | 5/2000 |
| GB | 1328591 | 8/1973 |

* cited by examiner

Primary Examiner—Thurman K. Page
Assistant Examiner—Rachel M. Bennett
(74) Attorney, Agent, or Firm—Klauber & Jackson

(57) ABSTRACT

The new galenic formulation of paracetamol is comprised of a base mixture of paracetamol and citric acid in a proportion of 85:15 to 90:10 w/w among other pharmaceutically acceptable components, in an exsiccation state corresponding to a water activity of less than 0.6 and it is in the form of a powder, granulate or tablet. The process comprises obtaining said exsiccated base mixture up to a water activity of less than 0.6 in order to obtain a powder, that can be granulated in order to obtain a granulate dispersible and soluble in water, whose granulate can also be compressed in order to obtain a tablet dispersible and soluble in water. Said new formulation is useful in human and veterinary medicine.

25 Claims, No Drawings

DISPERSIBLE AND SOLUBLE GALENIC PARACETAMOL FORMULATION, METHOD FOR ITS PREPARATION AND ITS APPLICATIONS

This application is a continuation of PCT/ES01/00402 filed Oct. 24, 2001.

TECHNICAL FIELD OF THE INVENTION

The present invention fits in the pharmaceutical sector and, more specifically in the field of the galenic formulation of analgesics, specifically paracetamol which is widely used in human medicine and veterinary medicine. The present invention provides a new galenic formulation of paracetamol with improved properties in comparison with the formulations presently existing on the market.

PRIOR ART

Paracetamol is N-(4-hydroxyphenyl) acetamide. It is a widely used analgesic that exists on the market under numerous brands in different galenic forms. Likewise, paracetamol is an active drug capable of being combined with other active ingredients for different uses. There are also numerous preparations on the market in which paracetamol is combined with other drugs. Therefore, there is a large number of pharmaceutical patents related to paracetamol.

According to the information provided by The Merck Index, 1996, 12$^{th}$ Ed., it is a product which in its pure form crystallizes from water in the form of large monoclinic prisms, has a melting point of 169–170.5° C. and a specific density at 21° C. of 1.293 g/cm$^3$. It has a maximum UV absorption (ethanol) at 250 nm with an ε of 13,800.

Paracetamol is a solid which is barely soluble in cold water, a solubility which increases considerably in hot water. Likewise, it is soluble in methanol, ethanol, dimethylformamide, ethylene dichloride, acetone and ethyl acetate. It is barely soluble in ether and practically insoluble in petroleum ether, pentane and benzene. Its $LD_{50}$ in mice (mg/Kg) is 338 when administered orally and 500 when its administration is interperitoneal.

Paracetamol is therapeutically catalogued as an analgesic and antipyretic, although at high doses it can also have anti-inflammatory action.

Paracetamol can be prepared from p-nitrophenol [Morse, Ber 11, 232 (1878); Tingle, Williams Am. Chem. J. 37, 63 (1907)], from p-amino-phenol [Lumiere et al., Bull. Soc. Chim. France [3] 33, 785 (1905); Fierz-Davil, Kuster, Helv. Chim. Acta 22, 94 (1939); Wilbert, De Angelis, U.S. Pat. No. 2,998,450 (1961 of Warner Lambert); Bergmann, German patent 453,577; Chem, Zentr. 1928.I, 2663; Frdl. 16, 238]; from p-hydroxyacetophenone hydrazone [Pearson et al., J. Am. Chem. Soc. 75, 5907 (1953)].

Data concerning its toxicity can be found in G. A. Starmer et al., Toxicol. Appl. Pharmacol 19, 20 (1971) and D. C. Dahlin, S. D. Nelson, J. Med. Chem. 25, 885 (1982); an evaluation of its effects on the kidneys can be found in D. P. Sandler et al. N. Engl. J. Med. 320, 1238 (1989); an extensive description of the product can be found in J. E. Fairbrother, Anal. Profiles Drug Subs. 3, 1-109 (1974); a compilation of its pharmacology can be found in B. Ameer, D. J. Greenblatt, Ann. Int. Med 87, 202–209 (1977); a compilation of studies regarding hepatotoxicity induced by paracetamol can be found in J. A. Hinson, Rev. Biochem. Toxicol. 2, 103–129 (1980); idem, Life Sci. 29, 107–116 (1981); and a compilation on protective agents is proposed in M. Davis, Sem. Liver. Dis. 6, 138–147 (1986).

European patent appln. no. 96942064, regarding formulations with a high paracetamol content, directly compressible, especially suitable to provide tablets with a high paracetamol content (>80%) with respect to the total weight of the tablet; and European patent E97936739 regarding stable liquid paracetamol formulations especially suitable to obtain antialgic injectable preparations; and European patent E90907166 regarding an ophthalmic paracetamol formulation and European patent 92301558 regarding compositions of sustained release of paracetamol among other drugs, can be cited among patents regarding special forms of paracetamol.

There are also numerous patents regarding pharmaceutical preparations in which paracetamol is combined with one or several active drugs, for different uses, among which the following stand out:

Spanish patent n° 530359 refers to the obtainment of an analgesic preparation made of paracetamol and tizamidine.

Spanish patent n° 551584 refers to the obtainment of a pharmaceutical preparation that contains flupirtine and paracetamol, especially appropriate for treating inflammatory diseases, degenerative articular diseases, arthrosis deformans, dysmenorrhea, post-operative pain, etc.

European patent application n° E90903746 refers to a preparation, among others, containing coumarin or calcium dibesilate and paracetamol, effective for treating arthrosis.

European patent application n° E92307474 refers to pharmaceutical cough preparations that comprise dextromethorphan and paracetamol.

European patent application n° E94908449 refers to pharmaceutical compositions that contain paracetamol and L-cysteine or a precursor thereof.

European patent application n° E95401290 refers to a powder-form formulation for drinkable solutions that contain metochlopramide and paracetamol, for uses in different therapies.

European patent application n° E95909789 refers to coated tablets that contain as active ingredients paracetamol and dompesidone (an antiemetic), with analgesic and antiemetic properties.

European patent application no. E96402580 refers to pharmaceutical compositions useful for treating migraines, compositions which contain paracetamol and metochlopramide.

Despite a lot of research, scientific publications and patents concerning paracetamol, it is certain that there is still not a galenic formulation thereof that is dispersible and soluble in water, with minimum effervescent effects and a high paracetamol content per pharmaceutical dose (tablet or packet of granulate) on the market.

Paracetamol has the physicochemical behavior characteristic of a fine powder barely soluble and dispersible in water. This is why the preparations currently existing on the market are practically insoluble and barely dispersible in cold water, which is the normal liquid medium which is used to swallow drugs. Only the Efferalgan brand tablets and effervescent packets of powder are soluble in cold water, but they do so rather slowly.

Nonetheless, it is well known that many consumers do not use effervescent preparations because they produce flatulence or prove to be unpleasant to take.

Besides, the weight ratio of paracetamol per dose in these cases is very low, because a rather large tablet, or a high granulate mass, is required in order to swallow a low dose of the active drug. This even makes it necessary to take two dose forms each time in order to achieve the threshold required for the desired effect.

Therefore, research still continues on new galenic formulations of paracetamol that overcome these inconveniences and that are easy to take.

The present inventors have focused their research efforts along these lines, achieving a new galenic formulation of paracetamol with excellent properties of dispersibility and solubility in cold water, which is the object of the present invention.

DETAILED DESCRIPTION OF THE INVENTION

As indicated in its title, the present invention refers to a new galenic formulation of paracetamol dispersible and soluble in water. The present invention also refers to the process for the preparation of said new formulation and to its pharmaceutical uses.

The new galenic formulation of the present invention essentially consists of paracetamol and citric acid, irrespective of the fact that it may include other types of products selected from among vehicles, binding agents, disaggregating agents, etc. commonly used in conventional pharmaceutical practice.

For the preparation of said formulation paracetamol is treated with a hot saturated citric acid solution, in a high speed mixer (at 500–1,000 rpm) for approximately 3–10 minutes, heating the mass to a temperature of about 45–55° C. Then, the stirring rate is reduced to approximately 10–120 rpm and a vacuum is applied to the mixing basin up to a pressure of approximately 10–30 mbar that contains a moist paracetamol and citric acid mass. Under these conditions, by effect of the latent heat of vaporization of the mass, the temperature thereof drops to about 30–35° C., which prevents degradation of the paracetamol. Besides, the citric acid tends to form its monohydrate, for which reason it sequesters the water from the mass during this drying period, making it possible to achieve a semi-dry state of the mass in which the water activity is less than 1 (Aw<1). Within the context of the present invention, the term semi-dry is understood as the property that the paracetamol:citric acid mass has to capture water forming hydrates at temperatures lower than 45–55° C. It is known that citric acid forms hydrates below this temperature, the free water becoming bound water. Therefore, the referred mass will have a moist appearance (Aw>1) at temperatures higher than 45° C., whereas below 45° C., the mass will have a dry appearance (Aw<1). The drying rate depends on the intensity of the vacuum applied, achieving faster drying as the vacuum increases, that is to say, when the pressure drops inside the basin.

The amounts of paracetamol and citric acid that are used in the mixture are 85–90% (weight/weight) of paracetamol and 15–10% (weight/weight) of citric acid. Citric acid is used in the form of a 55–60% (weight/volume) aqueous solution. In order to dissolve the citric acid in water, it is necessary to preheat it to 60–80° C., after which the citric acid is added under continuous stirring until it completely dissolves (the dissolving temperature of citric acid normally varies between 60 and 65° C.).

The product resulting from the above-cited process is a dry mass of paracetamol and citric acid in powder form. A dry mass is understood to be one that does not have adherence due to moisture. For this reason the Aw should be lower than 0.6 and the water content determined by the Karl-Fisher method should be lower than 2%

Said dry paracetamol:citric acid mass has an apparent density of approximately 0.6–0.8 g/ml. Besides, it is rapidly soluble in cold water (approximately at 12–20° C., which is the normal temperature of tap water). "Rapidly soluble" is understood to be when a dose of paracetamol of 500–1,000 mg dissolves in a proportion higher than 90%, in 60 ml of said cold water, with stirring, in less than 3 minutes.

Another characteristic of said dry mass is that its solution has a pH of 2.1–2.5 (measured by solubilizing 1 g thereof in 100 ml of cold water). Said dry mass in powder form constitutes the base mixture of the formulation of the present invention, which has excellent fluidity properties and a high compacting and compressing capacity. However, it has the inconvenience that its pH is too low, so as to be able to be used as such in highly dispersible soluble tablets.

In order to overcome this inconvenience, a weak alkali is added to the mass, together with an appropriate carrier. Hence, the composition of the formulation of the invention is essentially the following:

| Formulation I | weight (mg) per dose unit |
|---|---|
| Base mixture of paracetamol/citric acid (in a ratio of 85:15 to 90:10 % w/w) | 715–765 |
| Weak alkali    qsp pH | 5–5.5 |
| Pharmaceutically acceptable carrier | 3–6 |

The buffers sodium bicarbonate/sodium carbonate, sodium citrate alone or mixed with other weak organic acid salts are examples of the weak alkali that can be used.

In the event of using sodium bicarbonate/sodium carbonate, the amounts thereof would be of 15–30 mg and 2–10 mg, respectively, and in the event of using sodium citrate the amount thereof would be of 150–250 mg, all of these amounts referring to a dose unit.

The pharmaceutically acceptable carrier is selected among Sucroester 15, sodium lauryl sulfate and sodium ethyl sulfosuccinate.

This formulation, upon including bicarbonate and carbonate, in the presence of citric acid, has slightly effervescent properties when it comes in contact with water, for which reason it should be kept away from moisture during its handling and preservation.

However, the proportion of carbon anhydride that this mixture produces is minimum, if it is compared with that which is produced by the preparations currently existing on the market. Thus for example, while a dose of the mixture of the invention, corresponding to 650 mg of paracetamol gives off about 17–18 mg of $CO_2$, the effervescent preparations existing up until now give off approximately 550–650 mg of $CO_2$.

The above-described formulation I can be dosed directly in single dose packets for direct consumption as said powder, or else it can be subjected to a granulation process in order to obtain a granulated product. Said granulation process is carried out conventionally in a roller compactor.

The granulate thus obtained can be dosed in single dose packets, with some excellent dispersing and solubilizing characteristics of the granulate in cold water by gentle stirring by hand.

It is also possible to obtain tablets from the granulated product thus obtained. For this purpose, conventional products of galenic formulations in tablets, such as for example, taste correctors, sweeteners, flavoring agents, disaggregating agents, etc. can be added to the granulated mixture.

In accordance with the above, the starting formulation to obtain the tablet would essentially be the following:

| Formulation II | |
| --- | --- |
| | weight (mg) per dose unit |
| Paracetamol granulate | 735–811 |
| Flavor | 30–50 |
| Sweetener | 15–20 |
| Disaggregating agent | 15–20 |
| Lubricating agent | 10–20 |

Aspartame, saccharine, or mixtures thereof can be cited as examples of sweeteners. Crosspovidone, crosscaramellose or mixtures thereof can be mentioned as disaggregating agents. Magnesium stearate and/or polyethylene glycol can be used as examples of lubricating agents.

The tablet is obtained by direct dry compression of Formulation II.

The tablets obtained in accordance with the present invention are characterized in that they are soluble and weigh approximately 800–900 mg, which is approximately the weight of the unsoluble tablets currently existing on the market, for a dose of paracetamol of 500–650 mg Besides, they have the advantage of weighing less and being smaller than the presently marketed effervescent soluble tablets, that tend to weigh 2–5 g.

The tablets of the invention are additionally characterized in being stable at the temperature and moisture when they are packaged in a blister or jar, for a period of no less than 3 years; and in that they comply with the pharmacotechnical specifications for this type of drug, complying with the specifications for swallowable tablets as well as with the specifications for dispersible and soluble tablets. Therefore, the present invention presents tablets with the property of being swallowed directly or of being dispersed and solubilized in water in order to be taken. Obviously it has to be pointed out that the external disaggregating agent is not water soluble, but it represents a minimum amount of the total weight of the tablet (in the neighborhood of 15–20 mg).

The pharmacological advantage of the formulations of the invention is that since they are soluble, they provide a higher paracetamol absorption rate, which allows the symptoms to be alleviated much quicker.

The uses of the formulations of the present invention are the same as those of the other galenic preparations of paracetamol, and they are basically centered on its analgesic, antipyretic and anti-inflammatory activity useful in humans and animals, that is to say, in human medicine and veterinary medicine.

EMBODIMENTS OF THE INVENTION

The present invention is additionally illustrated by means of the following example, which in no way seeks to restrict its scope of protection.

EXAMPLE

A mixture of 1 kg of paracetamol and 225 ml of an aqueous 50% citric acid solution was prepared. The mixture was placed in the basin of a high speed mixer, where it was kept for 10 minutes, at a temperature of 45–55° C. (achieved by means of a heating sleeve at 65° C.) and subjected to a stirring rate of 600 rpm. After 10 minutes, the stirring rate is reduced to 120 rpm and the vacuum was produced in the basin up to a pressure of 10 mbars keeping the sleeve at 65° C., in order to dry the mixture until a water activity of less than 0.6 is achieved.

Then 720 mg of this dry paracetamol (650 mg) and citric acid (70 mg) mixture are mixed with 30 mg of sodium bicarbonate, 5 mg of sodium carbonate and 1 mg of sodium lauryl sulfate. The mixture thus obtained is subjected to a dry granulation process in a roller compactor with the following conditions:

Roller pressure: 90 KN

Feed: continuous

Cooling of the rollers: at 10–14° C.

Granulator sieve: 1.5 mm perforation diameter in order to obtain a granulate, that can be used as such, being dosed in single dose packets.

On the other hand, 756 mg of the granulate thus obtained are mixed with 50 mg of orange flavoring agent, 15 mg of aspartame and 15 mg of crosscaramellose and subjected to a direct dry compression process to obtain a tablet.

What is claimed is:

1. Galenic formulation of paracetamol dispersible and soluble in cold water comprising:

a base mixture of paracetamol and citric acid in a proportion between 85:15 and 90:10 w/w, having a water content of less than 2% as measured by the Karl-Fisher method, said formulation being in a form selected from the group consisting of a powder, a granulate, a tablet and in packets.

2. Formulation according to claim 1, wherein said base mixture has an apparent density, defined as the amount of mass of dry base mixture per unit of bulk volume, of 0.6–0.8 g/ml.

3. Formulation according to claim 1, wherein said base mixture has a solubility in cold water at 12–20° C. of 1 g/60 ml in 3 minutes, in a proportion higher than 90% of the mixture.

4. Formulation according to claim 1, wherein said base mixture has a pH in a solution of 2.1–2.5, measured by solubilizing 1 g thereof in 100 ml of cold water.

5. Formulation according to claim 1, comprising:

a base mixture of paracetamol and citric acid in a proportion between 85:15 and 90:10 w/w, having a water content of less than 2% as measured by the Karl-Fisher method, a weak alkali and pharmaceutically acceptable carrier.

6. Formulation according to claim 5, wherein its composition corresponds to Formulation I comprising per dose unit:

Base mixture of paracetamol/citric acid: 715–765 mg, weak alkali: sufficient quantity for obtaining a pH value between 5 and 5.5, pharmaceutically acceptable carrier: 3–6 mg.

7. Formulation according to claim 5, wherein said weak alkali is a buffer selected from the group formed by sodium bicarbonate/sodium carbonate, sodium citrate alone or mixed with one or more sodium or potassium salts of a pharmaceutically acceptable weak organic acid.

8. Formulation according to claim 6, said weak alkali is sodium bicarbonate/sodium carbonate and they are used in an amount of 15–30 mg and 2–10 mg per dose, respectively.

9. Formulation according to claim 6, wherein said weak alkali is sodium citrate and it is used in an amount of 150–250 mg, per dose unit.

10. Formulation according to claim 6, wherein said pharmaceutically acceptable carrier is selected from the group consisting of saccharose hexabutyrate acetate, sodium lauryl sulfate and sodium ethyl sulfosuccinate.

11. Formulation according to claim 6, wherein said formulation is in granulate form.

12. Formulation according to claim 6, wherein said formulation I, in granulate form, is mixed with one or several pharmaceutically acceptable taste correctors, sweeteners, flavoring agents, disaggregating agents and lubricating agents in order to obtain a Formulation II.

13. Formulation, according to claim 2, the composition of said Formulation II is the following:

| Formulation II | |
| --- | --- |
| | weight (mg) per dose unit |
| Paracetamol granulate | 735–811 |
| Flavor | 30–50 |
| Sweetener | 15–20 |
| Disaggregating agent | 15–20 |
| Lubricating agent | 10–20. |

14. Formulation according to claim 2, wherein said formulation is in the for of a tablet or in packets.

15. Process for the preparation of a galenic formulation of paracetamol of claim 12, said process comprising the steps of:
a) preparing an exsiccated base mixture comprised of paracetamol and citric acid, with a water content of less than 2% as measured by the Karl-Fisher method;
b) granulating the formulation in order to obtain a granulate dispersible and soluble in water;
c) compressing Formulation II containing said granulate, in order to obtain a tablet dispersible and soluble in water.

16. Process according to claim 15, wherein step a) is carried out by mixing paracetamol in an aqueous citric acid solution at a high rate and heating same.

17. Process according to claim 16, the relative proportions of paracetamol and citric acid that are mixed are 8:15 to 90:10% w/w.

18. Process according to claim 16, wherein the mixing is done at a rate of 500–1,000 rpm.

19. Process according to claim 16, wherein the mixing is carried out at a temperature of the mixture of 45–55° C.

20. Process according to claim 16, wherein the heating is carried out for 3–10 minutes.

21. Process according to claim 16, wherein once the heating has ended the mixture is subjected to a vacuum for exsiccation up to a water a water content of less than 2% as measured by the Karl-Fisher method.

22. Process according to claim 21, wherein a vacuum is applied such that the pressure reached is 10–30 mbars.

23. Process according to claim 15, wherein step b) is carried out by mixing the components of raid formulation and subjecting the mixture to a dry granulation process with a roller compactor.

24. Process according to claim 15, wherein step c) is carried out by mixing the components of paid Formulation II, and subjecting the mixture to a direct dry compression process.

25. Method for using the galenic formulation of paracetamol defined in claim 1, for the manufacturing of drugs with an analgesic, antipyretic, anti-inflammatory activity, or mixture thereof in human medicine or veterinary medicine.

* * * * *